United States Patent [19]

Boop et al.

[11] Patent Number: 4,610,822

[45] Date of Patent: Sep. 9, 1986

[54] PROCESS FOR PREPARING 6-[D(-)-α-(4-C$_1$-C$_4$)-ALKYL-2,3-DIOXO-1-PIPERAZINOCARBONYLAMINO)-PHENYLACETAMIDO]PENICILLANIC ACIDS

[75] Inventors: Donald C. Boop, Bloomsbury; Karel F. Bernady, Belle Mead, both of N.J.

[73] Assignee: American Cyanamid Company, Stamford, Conn.

[21] Appl. No.: 357,431

[22] Filed: Mar. 12, 1982

Related U.S. Application Data

[63] Continuation-in-part of Ser. No. 248,754, Mar. 30, 1981, abandoned.

[51] Int. Cl.$^4$ ............................................. C07D 499/04
[52] U.S. Cl. ...................................... 540/316; 540/333
[58] Field of Search ...................................... 260/239.1

[56] References Cited

U.S. PATENT DOCUMENTS 4,112,090 9/1978 Saikawa et al. ................ 260/239.1

*Primary Examiner*—Natalie Trousof
*Assistant Examiner*—Vera C. Clarke
*Attorney, Agent, or Firm*—M-E. M. Timbers

[57] ABSTRACT

Improved process for the preparation of 6-substituted penicillanic acids, in particular 6[D(-)-α-(4-alkyl-2,3-dioxo-]-piperazinocarbonylamino)phenylacetamido]-penicillanic acids, and the pharmaceutically acceptable salts thereof.

4 Claims, No Drawings

PROCESS FOR PREPARING 6-[D(-)-α-(4-$C_1$-$C_4$)-ALKYL-2,3-DIOXO-1-PIPERAZINOCARBONYLAMINO)-PHENYLACETAMIDO]PENICILLANIC ACIDS

This application is a continuation-in-part of application Ser. No. 248,754 filed on Mar. 30, 1981 and now abandoned.

BACKGROUND OF THE INVENTION

1. Field of Invention

The present invention relates to a novel improved process for the preparation of 6-substituted penicillanic acids. More particularly, it relates to an improved process for the preparation of 6-[D(-)-α-(4-alkyl-2,3-dioxo-]-piperazinocarboxylamino)phenylacetamido]penicillanic acids of Formula (I)

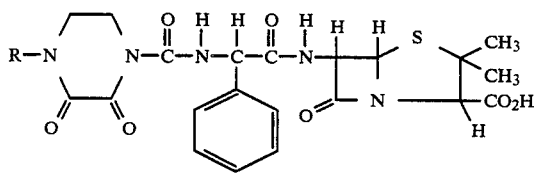

wherein R represents $C_1$-$C_4$ alkyl. These compounds are useful as antibiotics for the treatment of pneumonia, peritonitis, and blood system infections.

2. Description of Prior Art

Saikawa et al. disclose in U.S. Pat. No. 4,112,090 a process for preparing 6-substituted penicillanic acids of formula (I) by reacting a 4-$C_1$-$C_4$ alkyl-2,3-dioxo-1-piperazinocarbonyl chloride of Formula II

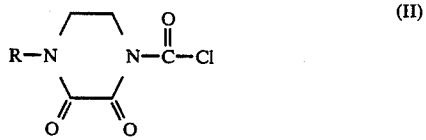

wherein R is $C_1$-$C_4$ alkyl, with 6-[D(-)-α-aminophenylacetamido]penicillanic acid trihydrate, commonly known as ampicillin trihydrate, represented by Formula (III).

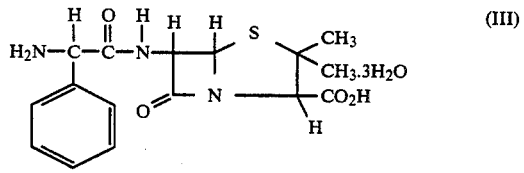

In Example 23 of this reference, a suspension of (III) in a mixture of 10 parts water and 4.5 parts by weight of ethyl acetate per part by weight of compound III is cooled to 2° C., admixed with 2 molar equivalents of potassium carbonate at 2°-3° C. for several minutes, admixed with 1 molar proportion of a compound of formula (II) wherein R is methyl at 2°-3° C. over a period of 10 minutes, and further reacted at said temperature for 15 minutes. The reaction mixture is clarified to remove some insolubles and the mother liquor is mixed with an additional 18 parts by weight of ethyl acetate per part by weight of compound III originally charged. The resulting mixture is then acidified with 1 molar equivalent of 2N HCl at 20°-22° C. over a period of 5 minutes, and stirred at 20°-22° C. for 5 hours. The crystals which precipitate are collected, washed successively with water and isopropanol, and dried to obtain a dihydrate of 6-[D(-)-α-(4-methyl-2,3-dioxo-1-piperazinocarbonylimino)phenylacetamido]penicillanic acid in a yield of 75.4%. In a similar example, a monohydrate of 6-[D(-)-α-(4-ethyl-2,3-dioxo-1-piperazinocarbonylamino)phenylacetamido]penicillanic acid is obtained in a yield of 84.8% with the compound of Formula (II) wherein R=ethyl.

There is a need for an improved process which significantly increases the yield obtained. The present invention provides such a process, with a final yield of about 95%.

SUMMARY OF THE INVENTION

The present invention provides an improvement in a process for preparing a 6-[D(-)-α-(4-$C_1$-$C_4$ alkyl-2,3-dioxo-1-piperazinocarbonylamino)phenylacetamido]penicillanic acid of Formula (I) wherein a 4-$C_1$-$C_4$ alkyl-2,3-dioxo-1-piperazinocarbonyl halide is added to a solution or suspension of ampicillin in a mixture of ethyl acetate and water in the presence of a base to form a reaction mixture, the resulting mixture is agitated until the reaction is completed, the reaction mixture is acidified, and a crystalline product is recovered therefrom; said improvement comprising:

(1) adding about 1-1.5 molar proportions of a 4-$C_1$-$C_4$ alkyl-2,3-dioxo-1-piperazinocarbonyl halide to an agitated suspension of about one molar proportion of ampicillin or ampicillin trihydrate and an appropriate amount of a suitable base in a solvent mixture consisting of about 9-12 parts by weight of water and about 0.5-8 parts by weight of ethyl acetate per part by weight of ampicillin, over a period of at least 30 minutes, at about 10°-25° C., while maintaining a pH of about 6-8.3;

(2) further agitating the reaction mixture at about 10°-25° C. for at least 15 minutes upon completing the addition of the 4-$C_1$-$C_4$ alkyl-2,3-dioxo-1-piperazinocarbonyl halide in step (1);

(3) adding to the reaction mixture about 0.05-0.2 part by weight each of an activated carbon and a filter-aid per part by weight of ampicillin charged in step (1), and agitating the resulting mixture at about 10°-25° C. for at least 10 minutes;

(4) clarifying the resulting mixture, and washing the insoluble materials with about 0.6-2.5 parts by weight of water per part by weight of ampicillin charged in step (1);

(5) combining the mother liquor and wash liquor obtained in step (4) with about 2-12.5 parts by weight of ethyl acetate per part by weight of ampicillin charged in step (1), with the proviso that the total amount of ethyl acetate used in steps (1) and (5) is about 10-13 parts by weight per part by weight of said ampicillin, and warming the resulting mixture to about 15°-25° C.;

(6) acidifying the mixture obtained in step (5) to about 15°-25° C. to a pH of about 2.0-2.5;

(7) agitating the acidified mixture for at least one hour at about 15°-25° C., before collecting the resulting crystalline product; and (8) optionally converting the product to a pharmaceutically acceptable salt.

The process of the present invention results in about a 95% yield of the product of Formula (I).

DETAILED DESCRIPTION OF THE INVENTION

In carrying out the process of this invention, a stirred suspension of ampicillin or ampicillin trihydate in a mixture of water and ethyl acetate is prepared in amounts to provide about 9-12, preferably about 10-11, parts by weight of water and about 0.5-8, preferably about 4-6, parts by weight of ethyl acetate per part by weight of ampicillin.

To this mixture is added an appropriate amount of a suitable base. In order to insure the high yields of the present invention, the amount of base must be sufficient to bring the pH of the initial mixture to about 6-8.3, preferably about 6.5-8, and to maintain the pH range during the subsequent addition of the 4-$C_1$-$C_4$ alkyl-2,3-dioxo-1-piperazinocarbonyl halide. The preferred method of adding base is to charge the initial mixture with about 2.4-3.0, preferably about 2.5-2.7, molecular equivalents of a base such as sodium or potassium bicarbonate per mole of ampicillin charged. With this method the subsequent addition of the carbonyl halide will not induce a pH change outside the acceptable range of 6-8.3. Alternatively, a base such as, e.g., potassium or sodium hydroxide or potassium or sodium carbonate may be used to bring the pH of the initial mixture to about 6-8.3, preferably about 6.5-8, but care must be taken thereafter to monitor the pH and to maintain this pH range during the subsequent addition of the carbonyl halide. The pH may be monitored by direct inspection and addition of appropriate acid or base or the pH may be maintained at the proper range by the addition to the initial reaction system of an appropriate non-interfering buffer system, which buffer system is readily determined by those skilled in the art.

The initial mixture is adjusted to a temperature of about 10°-25° C., preferably about 12°-18° C., to which is added about 1-1.5, preferably about 1.05-1.15, molecular proportions of a 4-$C_1$-$C_4$alkyl-2,3-dioxo-1-piperazinocarbonyl halide of the formula:

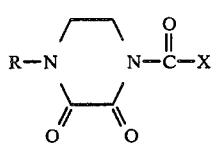

(IV)

wherein R is $C_1$-$C_4$ alkyl and X is fluoro, chloro, bromo, or iodo. The compound of Formula IV is added to the mixture over a period of at least 30 minutes, preferably over about 40-60 minutes, while maintaining the reaction mixture at the above-stated temperature and a pH of about 6-8.3, preferably about 6.5-8. In the preferred process the compound of Formula IV is 4-$C_1$-$C_4$ alkyl-2,3-dioxo-1-piperazinocarbonyl chloride; 4-ethyl-2,3-dioxo-1-piperazinocarbonyl chloride is particularly preferred.

The resulting mixture is stirred at said temperature and pH for at least 15 minutes; and preferably for about 20-30 minutes, after completion of the addition of the compound of Formula IV. The reaction mixture is then treated with about 0.05-0.2, preferably about 0.08-0.1, part by weight of an activated carbon such as, e.g., activated charcoal or Type RB Activated Carbon (Pittsburgh Coke and Chemical Co.), and about 0.05-0.2, preferably about 0.1-0.15, part by weight of a filter aid such as, e.g., Hyflo ® Super-Cel (Johns-Manville Sales Corp.), per part by weight of ampicillin originally charged. The resulting mixture is then stirred at said temperature for at least 10 minutes, and preferably for about 15-20 minutes.

The insolubles are then separated from the reaction mixture by conventional methods well known to those skilled in the art. The preferred method of separation is filtration. The filter cake is washed with about 0.6-2.5, preferably about 1.0-1.2, parts by weight of water per weight of ampicillin originally charged. The wash liquor is then combined with the mother liquor obtained from the filtration process and about 2-12.5, preferably about 6-7, parts by weight of ethyl acetate per part by weight of ampicillin originally charged is added thereto, with the proviso that the total amount of ethyl acetate used, including the ethyl acetate in the original reaction mixture, is about 10-13, preferably about 11-12, parts by weight per part by weight of ampicillin originally charged.

The resulting mixture is warmed to about 15°-25° C., preferably to about 18°-22° C., and acidified at said temperature to a pH of about 2.0-2.5, preferably about 2.2-2.3, with dilute mineral acid, e.g. 2-N hydrochloric or sulfuric acid.

The acidified reaction mixture is then stirred at said temperature for at least one hour, preferably for about 2-3 hours, and the resulting crystals are collected by means well known to those skilled in the art, such as, e.g., by filtration or centrifugation. The crystals are then washed with water and dried to obtain the desired free acid product in a yield of about 94-96%. This free acid may be hydrated in varying degrees.

The choice of ethyl acetate as a solvent is critical, as is the relative concentration of ethyl acetate during the crystallization step. Control of the pH during the reaction and crystallization stages is also critical. Variation of the stated ranges of these factors will either decrease the ultimate yield or result in an inferior crystallization structure, possibly even resulting in an amorphous mass with no crystalline structure at all, which makes isolation and purification of the final product time-consuming and expensive.

The free acid obtained above may be converted to a pharmaceutically acceptable salt by procedures well known to those skilled in the art. Pharmaceutically acceptable salts include, e.g., alkali emtal, alkaline earth metal, ammonium, N-methylglucamine, etc. The sodium salt is preferred and is preferably obtained by treatment of the compound of Formula (I) obtained by the above process with an equivalent amount of sodium bicarbonate in water.

As used hereinabove and below unless expressly stated to the contrary, all temperatures and temperature ranges refer to the centigrade system. The term percent or (%) refers to the weight percent and the terms mole and moles refer to gram moles. The term equivalent refers to a quantity of reagent equal in moles to the moles of the preceding or succeeding reactant cited in that particular preparation or example in terms of moles of finite weight or volume.

DESCRIPTION OF THE PREFERRED EMBODIMENT

The present invention also provides for a preferred improved process, wherein (1) about 1.05–1.15 molar proportions of the 4-$C_1$–$C_4$ alkyl-2,3-dioxo-1-piperazinocarbonyl halide of Formula IV is added to a suspension containing 2.5–2.7 molar equivalents of an appropriate base in a solvent mixture consisting of about 10–11 parts by weight of water and about 4–6 parts by weight of ethyl acetate per part by weight of ampicillin (or equivalent amount of ampicillin trihydrate), over a period of about 40–60 minutes at about 12°–18° C., while maintaining a pH of about 6.5–8;

(2) the reaction mixture is further agitated at about 12°–18° C. for about 20–30 minutes;

(3) the reaction mixture is treated with about 0.08–0.1 part by weight of an activated carbon and about 0.1–0.15 part by weight of a filter-aid per part by weight of ampicillin originally charged and the resulting mixture is agitated at about 12°–18° C. for about 15–20 minutes;

(4) after clarification, the insoluble materials are washed with about 1.0–1.2 parts by weight of water per part by weight of ampicillin;

(5) the mother liquor and wash liquor are combined with about 6–7 parts by weight of ethyl acetate per part by weight of ampicillin originally charged, and the resulting mixture is warmed to about 18°–22° C., with the proviso that the total amount of ethyl acetate used in steps (1) and (5) is about 11–12 parts by weight of ampicillin originally charged;

(6) the reaction mixture is acidified at about 18°–22° C. to a pH of about 2.2–2.3;

(7) the acidified reaction mixture is agitated at about 18°–22° C. for about 2–3 hours, before collecting the crystalline free acid; and (8) the free acid is optionally dissolved in water, preferably at a concentration of about 10–20%, most preferably at a concentration of about 13% (grams of anhydrous free acid/100 mls. of water) by gradually adding about one mole equivalent of alkali metal bicarbonate; the reaction mixture is stirred for 3–4 hours at 6°±4° C. until the pH drops to at least 6.5, before collecting the alkali metal salt of the product of Formula (I).

A further understanding of the invention can be had from the following non-limiting examples. All parts are by weight unless otherwise indicated.

EXAMPLE 1

Preparation of
6-[D(-)-α-(4-Ethyl-2,3-dioxo-1-piperazinocarbonylamino)phenylacetamido]penicillanic Acid Monohydrate To an agitated slurry of 27.00 grams of ampicillin trihydrate (equivalent to 22.86 grams (0.0654 mole) of real anhydrous ampicillin), 14.50 grams (0.1726 mole) of sodium bicarbonate, 238 grams of water, and 119 grams of ethyl acetate, all at 15±2° C., is added 14.73 grams (0.0720 mole) of 4-ethyl-2,3-dioxo-1-piperazinocarbonyl chloride at a rate to maintain a pH greater than 6 and a temperature of 15±2° C. Upon completion of the addition, the reaction mixture is agitated at 15±2° C. for 20 minutes, and 2.1 grams of activated carbon (Type RB Activated Carbon; Pittsburgh Coke and Chemical Company), and 3.0 grams of a filter-aid (Hyflo ® Super-Cel; Johns-Manville Sales Corp.) are added thereto. The mixture is stirred for an additional 10 minutes, and the solids are removed by filtration and washed with 26 grams of water. The filtrate and wash liquor are combined and then mixed with 142.5 grams of ethyl acetate. The temperature of the resulting mixture is adjusted to 20°–22° C., and the pH is adjusted to 2.3 by the addition of 2N hydrochloric acid thereto. The acidified mixture is agitated at 20°–22° C. for 2.5 hours and the crystalline precipitate is isolated by filtration, washed with 120 grams of water, and dried to obtain 33.49 grams (95.58% of theoretical) of the desired product.

EXAMPLE 2

Preparation of
6-[D(-)-α-(4-Ethyl-2,3-dioxo-1-piperazinocarbonylamino)phenyl acetamido]penicillanic Acid, Sodium Salt 13.5 g. of the product of Example 1 (0.025 moles, equivalent to 13.125 g. of the anhydrous free acid) is slurried in 100 milliliters of water, and to the stirred mixture at 6°4° C. is added 2.06 grams of sodium bicarbonate (0.025 moles, equivalent to 15.7% w/w of the anhydrous free acid) in 10 increments of 0.206 grams each. The reaction is allowed to proceed until the pH drops to at least 6.5, a period of 3–4 hours. The reaction mixture is sterilized by cold filtration, filled into asceptic vials and lyophilized to produce white or pale yellow crystals of 6-[D(-)-α-(4-ethyl-2,3-dioxo-1-piperazinocarbonylamino)phenylacetamido]penicillanic acid, sodium salt.

I claim:

1. In a process for preparing a 6-[D(-)-alpha-(4-$C_1$–$C_4$ alkyl-2,3-dioxo-1-piperazinocarbonylamino)-phenylacetamido]penicillanic acid wherein a 4-$C_1$–$C_4$ alkyl-2,3-dioxo-1-piperazinocarbonyl halide is added to a solution or suspension of ampicillin in a mixture of ethyl acetate and water in the presence of a base to form a reaction mixture, the resulting mixture is agitated until the reaction is completed, the reaction mixture is acidified, and a crystalline product is recovered therefrom; the improvement which comprises:

(a) adding about 1.05–1.15 molar proportions of the 4-ethyl-2,3-dioxo-1-piperazinocarbonyl halide to an agitated suspension of about one molar proportion of ampicillin or ampicillin trihydrate and about 2.5–2.7 molar equivalent of a base in a solvent mixture consisting of about 10–11 parts by weight of water and about 4–6 parts by weight of ethyl acetate per part by weight of ampicillin (or equivalent amount of ampicillin trihydrate) over a period of about 40–60 minutes at about 12°–18° C. while maintaining a pH of about 6.5–8;

(b) further agitating the reaction mixture at about 12°–18° C. for about 20–30 minutes upon completing the addition of the 4-ethyl-2,3-dioxo-1-piperazinocarbonyl halide in Step (a);

(c) adding to the reaction mixture about 0.08–0.1 part by weight of an activated carbon and about 0.1–0.15 part by weight of a filter-aid per part by weight of ampicillin charged in Step (a), and agitating the resulting mixture at about 12°–18° C. for about 15–20 minutes;

(d) clarifying the resulting mixture, and washing the insoluble materials with about 1.0–1.2 parts by weight of water per part by weight of ampicillin charged in Step (a);

(e) combining the mother liquor and wash liquor obtained in Step (d) with about 6–7 parts by weight of ethyl acetate per part by weight of ampicillin charged in Step (a), and the resulting mixture is warmed to about 18°–22° C., with the proviso that the total amount of ethyl acetate used in Steps (a) and (e) is about 11–12 parts by weight per part by weight of said ampicillin;

(f) acidifying the mixture obtained in Step (e) at about 18°–22° C. to a pH of about 2.2–2.3;

(g) agitating the acidified mixture for at least one hour at about 18°–22° C. for about 2–3 hours before the crystalline free acid is collected, washed with water and dried; and (h) optionally converting the free acid to a pharmaceutically acceptable salt.

2. The process of claim 1, wherein the 4-ethyl-2,3-dioxo-1-piperazinocarbonyl halide is 4-ethyl-2,3-dioxo-1-piperazinocarbonyl chloride.

3. The process of claim 1, wherein the product is converted to the sodium salt.

4. The process of claim 1, wherein the 4-ethyl-2,3-dioxo-1-piperazinocarbonyl halide is 4-ethyl-2,3-dioxo-1-piperazinocarbonyl chloride converted to the sodium salt.

* * * * *

UNITED STATES PATENT OFFICE
CERTIFICATE OF CORRECTION

Patent No. 4,610,822　　　　Dated　September 9, 1986

Inventor(s)　Donald C. BOOP and Karel F. BERNADY

It is certified that error appears in the above-identified patent and that said Letters Patent are hereby corrected as shown below:

In Col. 1, ln. 17 should read:

"1-piperazinocarboxylamino)phenylacetamido]penicil-".

In Col. 4, ln. 25 should read:

"2.2-2.3, with dilute mineral acid, e.g. 2-5N hydrochloric".

Signed and Sealed this

Tenth Day of March, 1987

Attest:

DONALD J. QUIGG

Attesting Officer

Commissioner of Patents and Trademarks